(12) United States Patent
Kim et al.

(10) Patent No.: US 9,316,598 B2
(45) Date of Patent: Apr. 19, 2016

(54) METHOD OF DETECTING FOREIGN MATERIAL ON UPPER SURFACE OF TRANSPARENT SUBSTRATE USING POLARIZED LIGHT

(71) Applicant: Nanoprotech Co., Ltd., Daejeon (KR)

(72) Inventors: Yeong Ryeol Kim, Daejeon (KR); Cheul Ock Chae, Gunsan-si (KR); Jin Yong Kim, Daejeon (KR); Sang Tae Kim, Cheonan-si (KR)

(73) Assignee: Nanoprotech Co., Ltd., Daejeon (KR)

( * ) Notice: Subject to any disclaimer, the term of this patent is extended or adjusted under 35 U.S.C. 154(b) by 0 days.

(21) Appl. No.: 14/657,187

(22) Filed: Mar. 13, 2015

(65) Prior Publication Data

US 2015/0316492 A1 Nov. 5, 2015

(30) Foreign Application Priority Data

Apr. 30, 2014 (KR) .................. 10-2014-0052442

(51) Int. Cl.
*G01N 21/94* (2006.01)
*G01N 21/958* (2006.01)

(52) U.S. Cl.
CPC .............. *G01N 21/94* (2013.01); *G01N 21/958* (2013.01)

(58) Field of Classification Search
CPC .............................. G01N 21/94; G01N 21/958
USPC .................. 356/237.1–5, 369; 382/145, 147; 348/87, 129, 130
See application file for complete search history.

(56) References Cited

U.S. PATENT DOCUMENTS

| | | | |
|---|---|---|---|
| 8,027,036 B2 * | 9/2011 | Kim et al. ...................... | 356/337 |
| 2002/0145732 A1 * | 10/2002 | Vaez-Iravani et al. ..... | 356/237.2 |
| 2004/0051870 A1 * | 3/2004 | Sandberg et al. ............. | 356/338 |
| 2006/0001877 A1 * | 1/2006 | Moriya ......................... | 356/369 |
| 2007/0177136 A1 * | 8/2007 | Nakano et al. ............. | 356/237.2 |
| 2008/0055574 A1 * | 3/2008 | Kamono ......................... | 355/30 |
| 2009/0161943 A1 * | 6/2009 | Yamashita et al. ............ | 382/149 |
| 2011/0187849 A1 * | 8/2011 | Kim et al. .................... | 348/131 |
| 2012/0086800 A1 * | 4/2012 | Vladimirsky et al. ........ | 348/128 |

FOREIGN PATENT DOCUMENTS

| | | | |
|---|---|---|---|
| JP | 05196579 A | 8/1993 | |
| JP | 07-260295 A | 10/1995 | |

* cited by examiner

*Primary Examiner* — Hoa Pham
*Assistant Examiner* — Sunghee Y Gray
(74) *Attorney, Agent, or Firm* — The Webb Law Firm

(57) ABSTRACT

Provided are an apparatus and a method of detecting a foreign material capable of detecting only a foreign material on a surface of a substrate except for a foreign material on a lower surface of the substrate in a manufacturing process of a transparent substrate passing light therethrough, such as a glass substrate used in a flat panel display (FPD) such as a liquid crystal display (LCD), an organic light emitting diode (OLED), a plasma display panel (PDP), a sapphire wafer used in some of semiconductors, or the like, and in a pattern forming process in a manufacturing process of the FPD and the semiconductor using the transparent substrate.

3 Claims, 8 Drawing Sheets

METHOD OF DETECTING FOREIGN MATERIAL ON UPPER SURFACE OF TRANSPARENT SUBSTRATE USING POLARIZED LIGHT

CROSS-REFERENCE TO RELATED APPLICATION

This application claims priority to Korean Patent Application No. 10-2014-0052442, filed Apr. 30, 2014, the disclosure of which is hereby incorporated in its entirety by reference.

TECHNICAL FIELD

The present invention relates to an apparatus and a method of detecting a foreign material capable of detecting only a foreign material on a upper surface of a substrate except for a foreign material on a lower surface of the substrate in a manufacturing process of a transparent substrate passing light therethrough, such as a glass substrate used in a flat panel display (FPD) such as a liquid crystal display (LCD), an organic light emitting diode (OLED), a plasma display panel (PDP), etc., a sapphire wafer used in some of semiconductors, or the like, and in a pattern forming process in a manufacturing process of the FPD and the semiconductor using the transparent substrate.

BACKGROUND

Foreign materials may be generated due to several reasons in a manufacturing process of a transparent substrate having a thin thickness, a packaging process, a pattern forming process using the transparent substrate, and the like. In the case in which the foreign materials generated in these process environments are attached onto an upper surface of the substrate, they hinder fine patterns for pixels from being formed on the upper surface in the subsequent process to allow circuit patterns for forming the pixels not to be formed at corresponding positions, thereby causing defective pixels and decreasing a process yield. Therefore, a process of inspecting the foreign materials on the upper surface of the substrate should be performed during or after the manufacturing process.

A lower surface of the substrate contacts a transporting means in order to transport the substrate in a manufacturing process of a flat panel display (FPD) and a semiconductor. Therefore, much more foreign materials may be attached onto the lower surface of the substrate than onto the upper surface of the substrate. Since fine materials having sizes smaller than those of pixels among the foreign materials on the lower surface of the substrate do not have an influence on characteristics of the pixels, the fine foreign materials on the lower surface of the substrate are permitted. Therefore, only the foreign materials on the upper surface of the substrate have been strictly inspected in the manufacturing process of the transparent substrate and the manufacturing process of the FPD and the semiconductor using the transparent substrate.

In the manufacturing process of the FPD and the semiconductor, in order to inspect the foreign materials, a vision inspection method using an image obtained by irradiating light and imaging reflected light by a camera among non-contact inspection methods that do not damage the surface of the substrate has been mainly used. In the case of using the transparent substrate, the light arrives at the lower surface of the transparent substrate, such that reflected light on the foreign materials on the lower surface is also transferred. Therefore, the foreign materials on the lower surface are imaged, thereby making it possible to make an excessive badness decision and have an influence on a manufacturing yield. Therefore, a method of inspecting only the foreign material on the upper surface without being affected by the foreign materials on the lower surface has been required.

A schematic view of an apparatus 10 of detecting a foreign material according to the related art is shown in FIG. 1. Existing methods of detecting a foreign material T1 on an upper surface of a transparent substrate 14 will be described with reference to FIG. 1. There is a method of obliquely irradiating light L having a width enough to be irradiated to both of upper and lower surfaces of the transparent substrate to allow reflected light R to be imaged on foreign materials T1 and T2 on the upper and lower surfaces of the transparent substrate 14, setting a focus of a single imaging device for detection on the upper surface of the transparent substrate 14 and allowing a depth of an imaging lens to be smaller than a thickness of the transparent substrate to allow the foreign material T1 on the upper surface to be clearly viewed and allow the foreign material T2 on the lower surface to be obscurely viewed, thereby separating the foreign material T2 on the lower surface using a contrast difference between the foreign material T1 on the upper surface and the foreign material T2 on the lower surface. Since a contrast difference enough to distinguish an image of the foreign material T1 on the upper surface and an image of the foreign material T2 on the lower surface from each other should be present in order to apply this method, an imaging magnification should be raised or a thickness of the transparent substrate 14 should be thick. In the case of using a high imaging magnification, an inspection visual field is decreased, such that an inspection time becomes excessively long. In addition, in the case of inspecting a thin substrate, a contrast difference is not present, such that it may not be used.

A schematic view of an apparatus 20 of detecting a foreign material according to another exemplary embodiment of the related art is shown in FIG. 2. As shown, the apparatus 20 of detecting a foreign material uses a method of irradiating inclined light L, particularly, a light source having a very narrow width to make light irradiating positions on upper and lower surfaces of a transparent substrate 24 different from each other and then disposing visual fields of a camera 21 for imaging the upper surface and a camera 22 for imaging the lower surface at different positions to distinguish a foreign material T1 on the upper surface and a foreign material T2 on the lower surface from each other. In the case of this method, since the visual fields of the respective cameras 21 and 22 are different from each other, cameras having a lower magnification may be used, such that an inspection time may be decreased. However, also in this method, in the case of a thin substrate, since a distance between light irradiating positions becomes narrow, in the case in which the substrate vertically vibrates by a mechanism for transporting the transparent substrate 24, or the like, the light irradiating positions are horizontally changed, such that an image of the foreign material T2 on the lower surface is captured by the camera 21 for imaging the upper surface. Therefore, this method may also not be applied.

Therefore, a method of removing or significantly decreasing reflected light on the foreign material on the lower surface by allowing inspection light not to arrive at the lower surface has also been used. Japanese Patent Laid-Open Publication No. 1993-196579 has disclosed an apparatus of inspecting a foreign material on a glass substrate used in a manufacturing process of a liquid crystal panel, and more particularly, an apparatus of inspecting only a foreign material on a surface using light having a wavelength at which it is not transmitted through the glass substrate or light having a wavelength at which it has a low transmittance. This technology has an advantage that only the foreign material on the surface of the glass substrate is detected, but has a disadvantage that an expensive laser generating apparatus such as an Excimer laser, a CO2 laser, or the like, is required.

RELATED ART DOCUMENT

Patent Document

Japanese Patent Application Publication No. 05-196579 published on Aug. 6, 1993

SUMMARY

An object of the present invention is to provide an apparatus and a method of detecting a foreign material on an upper surface of a transparent substrate using polarized light capable of distinguishing a foreign material on a surface of the transparent substrate and a foreign material on a lower surface of the transparent substrate from each other and detecting them by detecting a difference between P-polarized light and S-polarized light scattered on the foreign material on the surface of the transparent substrate and P-polarized light and S-polarized light transmitted through the transparent substrate and then scattered on the foreign material on the lower surface of the transparent substrate in consideration of the fact that transmittances of P-polarized light and S-polarized light are different from each other.

Particularly, an object of the present invention is to provide an apparatus and a method of detecting a foreign material on an upper surface of a transparent substrate using polarized light capable of increasing detection accuracy by irradiating a light source at an incident angle at in which a difference between transmittances of P-polarized light and S-polarized light varied depending on an incident angle of the light source is large.

In one general aspect, an apparatus of detecting a foreign material on an upper surface of a transparent substrate using polarized light includes: a light source part irradiating light to the transparent substrate; a first detecting part detecting P-polarized light in scattered light of foreign materials attached onto the transparent substrate by the irradiated light; a second detecting part detecting S-polarized light in the scattered light of the foreign materials attached onto the transparent substrate by the irradiated light; and a controlling part comparing a brightness of the P-polarized light detected by the first detecting part and a brightness of the S-polarized light detected by the second detecting part with each other to distinguish the foreign material attached onto the upper surface of the transparent substrate and a foreign material attached onto a lower surface of the transparent substrate from each other.

An incident angle of the light irradiated to the transparent substrate may be 65 to 80 degrees.

The first detecting part may include a P-polarized light plate so as to detect only the P-polarized light, and the second detecting part may include an S-polarized light plate so as to detect only the S-polarized light.

The apparatus of detecting a foreign material on an upper surface of a transparent substrate using polarized light may further include a polarized light beam splitter (PBS) splitting the scattered light into the P-polarized light and the S-polarized light and irradiating the P-polarized light and the S-polarized light to a P-polarized light detector and a S-polarized light detector, respectively.

The light source part may include a non-polarized light source irradiating non-polarized light to the transparent substrate.

The light source part may include: a linearly polarized light source irradiating linearly polarized light to the transparent substrate; and a wavelength plate adjusting a polarized light angle of the linearly polarized light.

In another general aspect, a method of detecting a foreign material on an upper surface of a transparent substrate using polarized light includes: irradiating light having a predetermined incident angle to the transparent substrate; detecting P-polarized light in scattered light of foreign materials attached onto the transparent substrate by the irradiated light; detecting S-polarized light in the scattered light of the foreign materials attached onto the transparent substrate by the irradiated light; comparing a brightness of the P-polarized light and a brightness of the S-polarized light with each other to distinguish the foreign material attached onto the upper surface of the transparent substrate and a foreign material attached onto a lower surface of the transparent substrate from each other; and removing the foreign material attached onto the lower surface of the transparent substrate.

In the case in which the brightness of the P-polarized light and the brightness of the S-polarized light are the same as each other, it may be judged that the foreign material is the foreign material attached onto the upper surface of the transparent substrate, and in the case in which the brightness of the S-polarized light is darker than that of the P-polarized light, it may be judged that the foreign material is the foreign material attached onto the lower surface of the transparent substrate.

The method of detecting a foreign material on an upper surface of a transparent substrate using polarized light may further include correcting a P-polarized light detector detecting the P-polarized light and an S-polarized light detector detecting the S-polarized light so that the brightnesses of the P-polarized light and the S-polarized light scattered on the upper surface of the transparent substrate become the same as each other.

An incident angle of the light irradiated to the transparent substrate may be 65 to 80 degrees.

Since the apparatus and the method of detecting a foreign material on an upper surface of a transparent substrate using polarized light according to the present invention having the configuration as described above observe a wide visual field region to detect foreign materials unlike an apparatus of limiting a visual field to a narrow region to distinguish foreign materials, irradiated light or the foreign material does not escape from a visual field of the detecting apparatus even though vibrations occur at the time of transferring a substrate, thereby making it possible to accurately detect the foreign material.

In addition, since accurate alignment between a light source and a camera is not required, apparatuses, a cost, and a time required for the alignment at the time of installing the light source and the camera may be saved, and misalignment due to a change in an inclination during using the apparatus does not need to be corrected.

Further, since separate cameras are used in order to detect foreign materials on upper and lower surfaces to set focuses on the upper and lower surfaces, respectively, the apparatus of detecting a foreign material on an upper surface of a transparent substrate using polarized light may be used regardless of a thickness of the substrate, and since a visual field of the camera may be widened, an inspection time may be decreased.

Furthermore, since a general visible ray source or a cheap visible ray band laser may be used instead of an expensive special laser, the apparatus may be configured at a lower cost.

BRIEF DESCRIPTION OF THE DRAWINGS

The above and other objects, features and advantages of the present invention will become apparent from the following description of preferred embodiments given in conjunction with the accompanying drawings, in which.

[Detailed Description of Main Elements]

| | |
|---|---|
| 1000: Detecting apparatus | |
| 100: Light source par | 110: Light source |
| 120: Wavelength plate | 130: Reflecting plate |
| 200: First detecting part | 210: P-polarized light detector |
| 220: P-polarized light plate | |
| 300: Second detecting part | |
| 310: S-polarized light detector | |
| 320: S-polarized light plate | |
| 500: Stage | |
| S: Substrate | |
| P1, P2: Scattered P-polarized light | |
| S1, S2: Scattered S-polarized light | |
| T1: Foreign material on upper surface | |
| T2: Foreign material on lower surface | |

DETAILED DESCRIPTION OF EMBODIMENTS

Hereinafter, an exemplary embodiment of the present invention will be described in detail with reference to the accompanying drawings.

Figure 1:
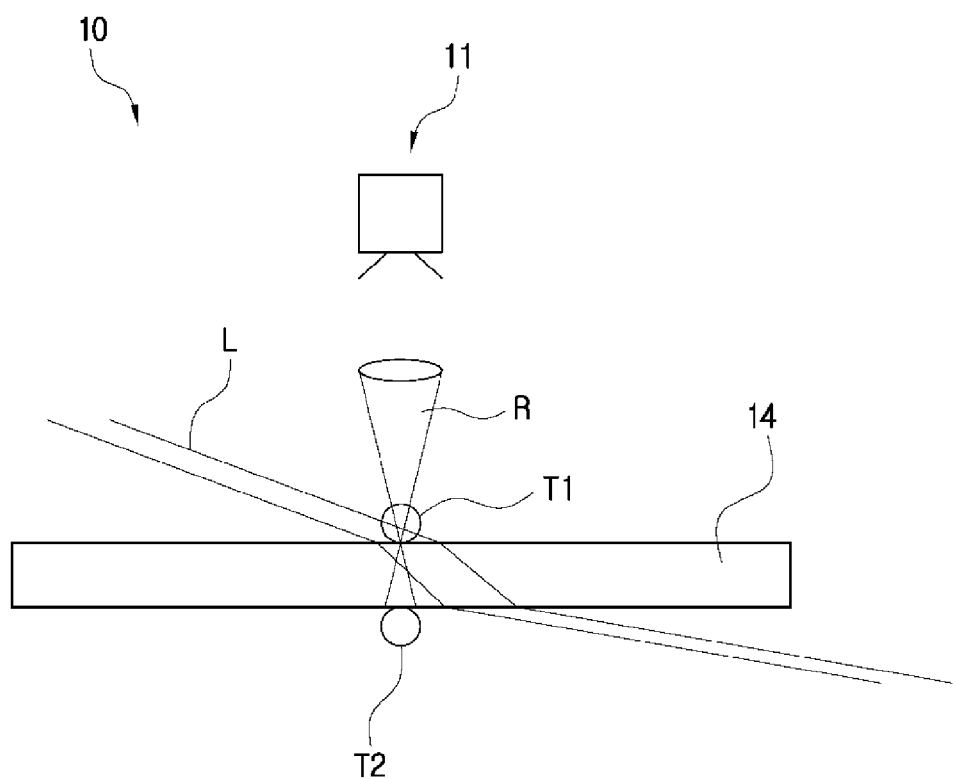
FIG. 1 is a schematic view of an apparatus of detecting a foreign material according to the related art.
Figure 2:
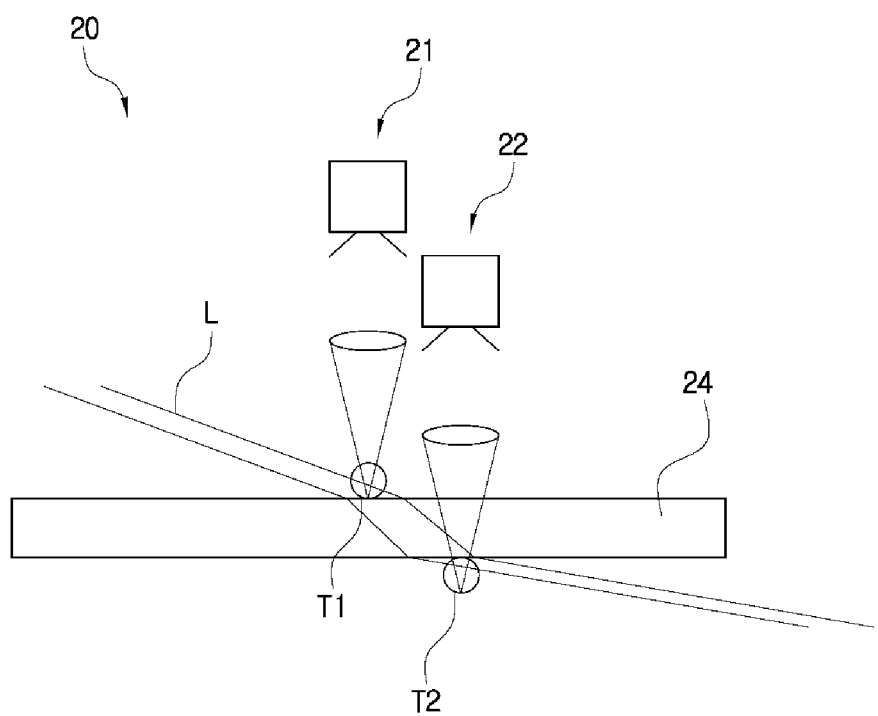
FIG. 2 is a schematic view of an apparatus of detecting a foreign material according to another exemplary embodiment of the related art.
Figure 3:
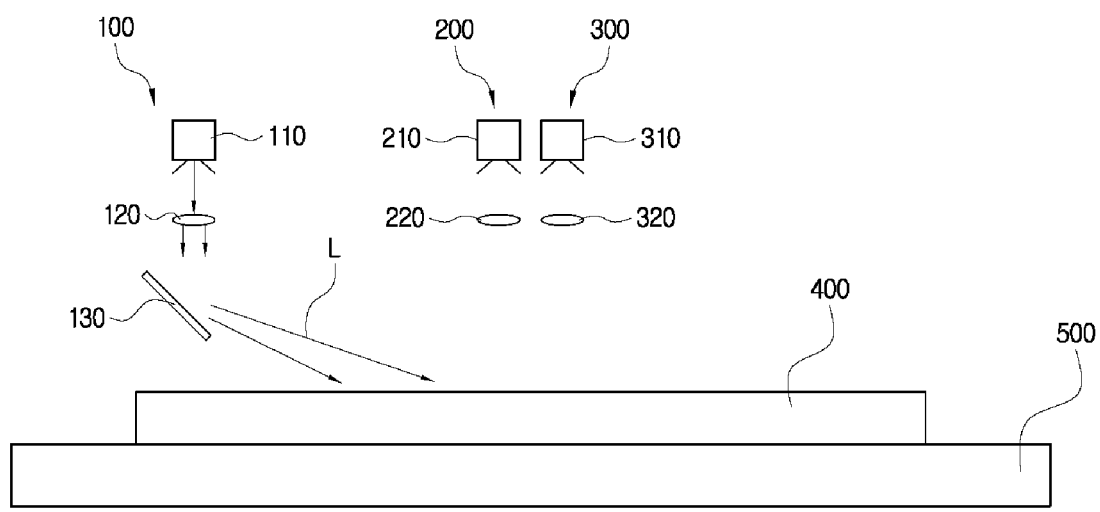
FIG. 3 is a schematic view of a detecting apparatus according to an exemplary embodiment of the present invention.

A schematic view of an apparatus 1000 of detecting a foreign material on an upper surface of a transparent substrate using polarized light according to an exemplary embodiment of the present invention (hereinafter, referred to as a 'detecting apparatus') is shown in FIG. 3. As shown, the detecting apparatus 1000 is configured to include a light source part 100, a first detecting part 200, a second detecting part 300, and a stage 500.

The light source part 100, which is a component for irradiating light to a substrate S, is configured to include a non-polarized light source irradiating non-polarized light to the substrate. In another exemplary embodiment, the light source part 100 includes a linearly polarized light source 110 irradiating linearly polarized light such as laser in order to irradiate a strong incident light amount as shown in FIG. 3. In the case in which the light source part 100 includes the linearly polarized light source 110, it further includes a wavelength plate 120 adjusting a polarized light angle of the linearly polarized light. A reflecting plate 130 is further included so that the light irradiated from the light source part 100 is irradiated to the substrate S at a predetermined incident angle.

The stage 500 is configured in order to support or transfer the substrate S for detecting a foreign material.

The first detecting part 200 is configured in order to detect scattered light of the light irradiated to the substrate S. Here, the first detecting part 200 is configured to detect P-polarized light in the scattered light. Therefore, the first detecting part 200 may be configured to include a P-polarized light detector 210 and a P-polarized light plate 220.

The second detecting part 300 is configured in order to detect scattered light of the light irradiated to the substrate S. Here, the second detecting part 300 is configured to detect S-polarized light in the scattered light. Therefore, the second detecting part 300 may be configured to include an S-polarized light detector 310 and an S-polarized light plate 320.

Although not shown in FIG. 3, in a detecting apparatus 1000 according to another exemplary embodiment, a polarized light beam splitter (PBS) splitting the scattered light into P-polarized light and S-polarized light and irradiating the P-polarized light and the S-polarized light to the P-polarized light detector 210 and the S-polarized light detector 310, respectively, may be configured, and the P-polarized light plate 220 and the S-polarized light plate 320 may be omitted.

When the light is irradiated in a state in which a foreign material is not present on the substrate S, the light passes through the substrate S as it is, such that the scattered light is not generated, and is not detected by the first and second detecting parts 200 and 300 having the configuration as described above, and it is judged by a controlling part judging detection signals of the first and second detecting parts 200 and 300 that the foreign material is not present on the substrate S.

On the other hand, when the light is irradiated in a state in which the foreign material is attached onto an upper surface or a lower surface of the substrate S, the scattered light is generated on the foreign material by the irradiated light and is detected by the first or second detecting part 200 or 300, and it is judged by the controlling part judging the detection signals of the first and second detecting parts 200 and 300 that the foreign material has been detected on the substrate S.

Here, the detecting apparatus 1000 according to the present invention is characterized in that a foreign material attached onto the upper surface of the substrate S and a foreign material attached onto the lower surface of the substrate S are accurately distinguished from each other using P-polarized light and S-polarized light of the scattered light and only the foreign material attached onto the upper surface is clearly detected. Next, a detailed configuration for implementing the above-configuration will be described in detail with reference to the accompanying drawings.

First, the P-polarized light means linearly polarized light in which a vibration direction of an electrical vector of light incident to a sample surface is included in an incident surface, and the S-polarized light means linearly polarized light in which a vibration direction of an electrical vector of light incident to the sample surface is perpendicular to the incident surface. Transmittances of the P-polarized light and the S-polarized light depending on an incident angle at which the P-polarized light and the S-polarized light are incident to the sample surface are different from each other and are shown in FIG. 4.

(See Optics (4th Edition) Eq4.42~4.45, Eq 4.61~4.64, Eugene Hecht, Addison Wesley)

Figure 4:
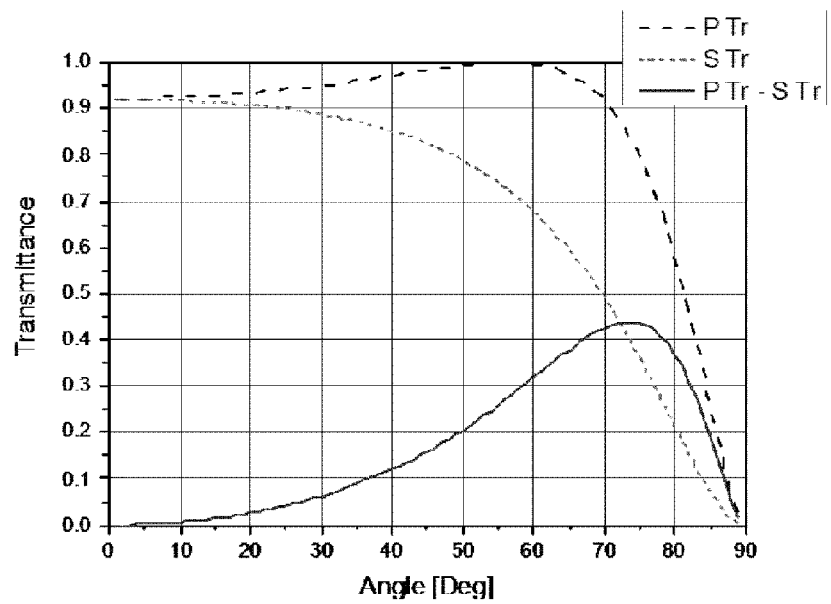
FIG. 4 is a graph showing transmittances of P-polarized light and S-polarized light depending on an incident angle of light.

A graph showing transmittances of P-polarized light and S-polarized light depending on an incident angle of light is shown in FIG. 4. As shown, it may be appreciated that a difference between the transmittances of P-polarized light and S-polarized light is large at an incident angle of 65 to 80 degrees and is the largest at an incident angle of 73 degrees.

The present invention has been configured in order to distinguish the foreign material attached onto the upper surface of the substrate S and the foreign material attached onto the lower surface of the substrate S from each other by comparing brightnesses of the P-polarized light and the S-polarized light scattered on the foreign material with each other in consideration of the characteristics of the P-polarized light and the S-polarized light as described above.

Figure 5:
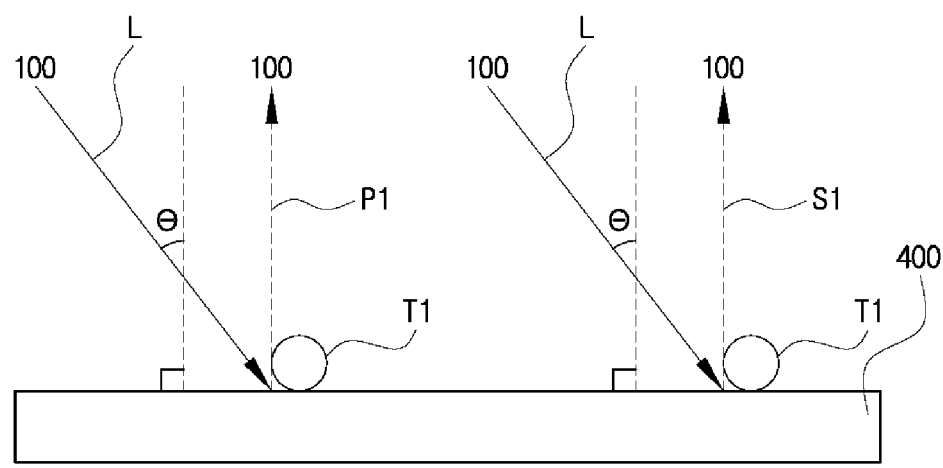
FIG. 5 is a schematic view showing P-polarized light and S-polarized light scattered on a foreign material on an upper surface of a substrate.
Figure 6:
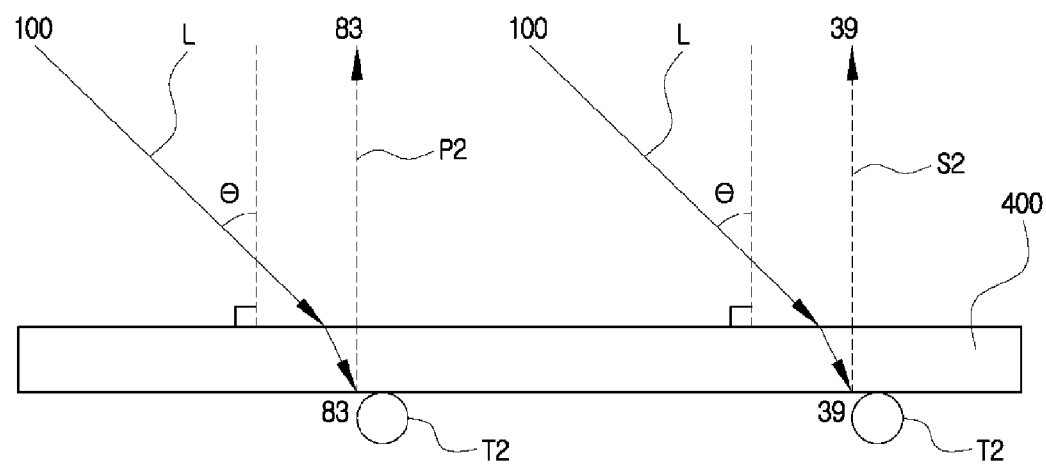
FIG. 6 is a schematic view showing P-polarized light and S-polarized light scattered on a foreign material on a lower surface of a substrate.

A schematic view of P-polarized light P1 (the left side of FIG. 5) scattered in a state in which it is not transmitted through the substrate S and S-polarized light S1 (the right side of FIG. 5) scattered in a state in which it is not transmitted through the substrate S is shown in FIG. 5.

As shown, when it is assumed that a brightness of light incident at a predetermined incident angle θ is 100, in the case in which the incident angle θ is 73 degrees, a brightness of the scattered P-polarized light P1 also becomes 100. In addition, when it is assumed that a brightness of light incident at a predetermined incident angle θ is 100, in the case in which the incident angle θ is 73 degrees, a brightness of the scattered S-polarized light S1 also becomes 100.

As shown, when it is assumed that a brightness of light incident at a predetermined incident angle θ is 100, in the case in which the incident angle θ is 73 degrees, a brightness of the P-polarized light P2 scattered in the state in which it is transmitted through the substrate S becomes 83. In addition, when it is assumed that a brightness of light incident at a predetermined incident angle θ is 100, in the case in which the incident angle θ is 73 degrees, a brightness of the S-polarized light S2 scattered in the state in which it is transmitted through the substrate S becomes 39.

That is, the brightnesses of the P-polarized light P1 and the S-polarized light S1 scattered on the upper surface of the substrate S are the same as each other, and the brightnesses of the P-polarized light P2 and the S-polarized light S2 transmitted through the substrate S and scattered on the lower surface of the substrate S are different from each other. (The brightness of the S-polarized light S2 is two times or more darker than that of the P-polarized light P2)

Therefore, since the brightnesses of the P-polarized light and the S-polarized light scattered on the foreign material attached onto the upper surface of the substrate S are the same as each other and the brightnesses of the P-polarized light and the S-polarized light scattered on the foreign material attached onto the lower surface of the substrate S are different from each other, the foreign material attached onto the upper surface of the substrate S and the foreign material attached onto the lower surface of the substrate S may be accurately distinguished from each other using the above-mentioned difference.

Figure 7:
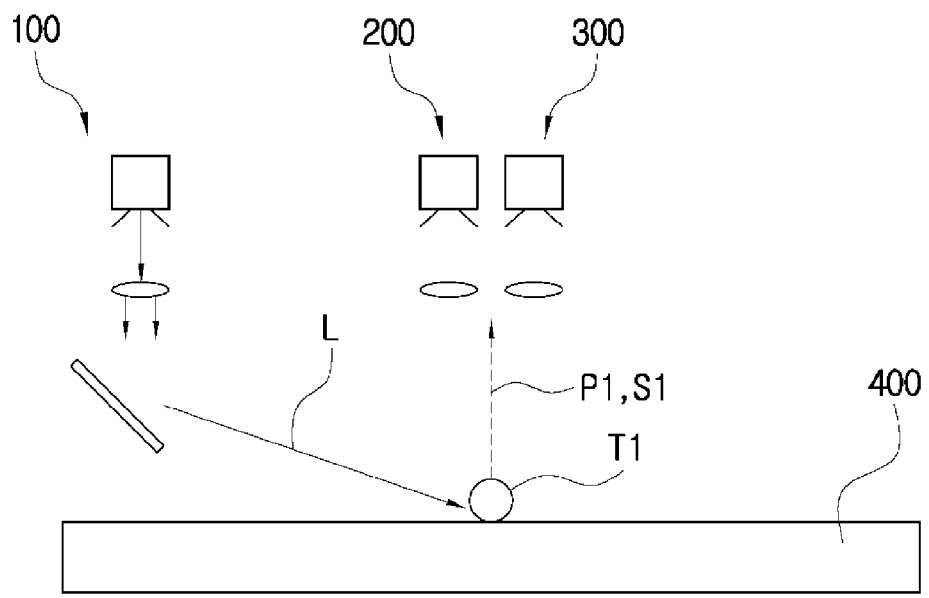
FIG. 7 is a schematic view at the time of detecting the foreign material on the upper surface using the detecting apparatus according to an exemplary embodiment of the present invention.
Figure 8A:
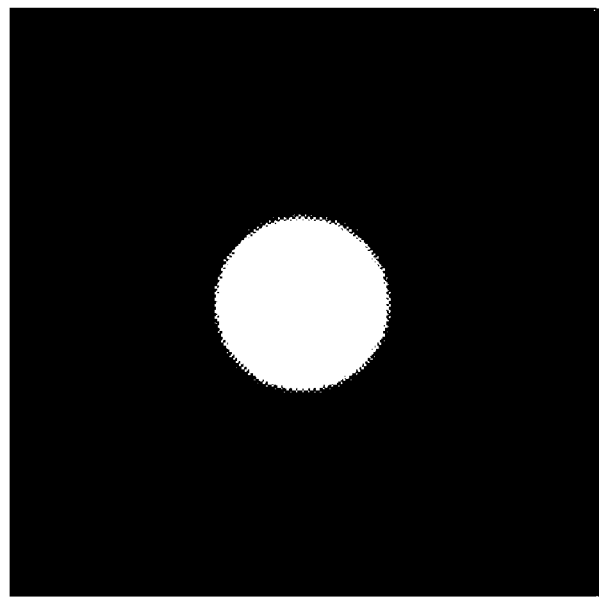
FIGS. 8a and 8b are photographed images of foreign materials detected through a P-polarized light detector and an S-polarized light detector at the time of detecting the foreign material on the upper surface.
Figure 8B:
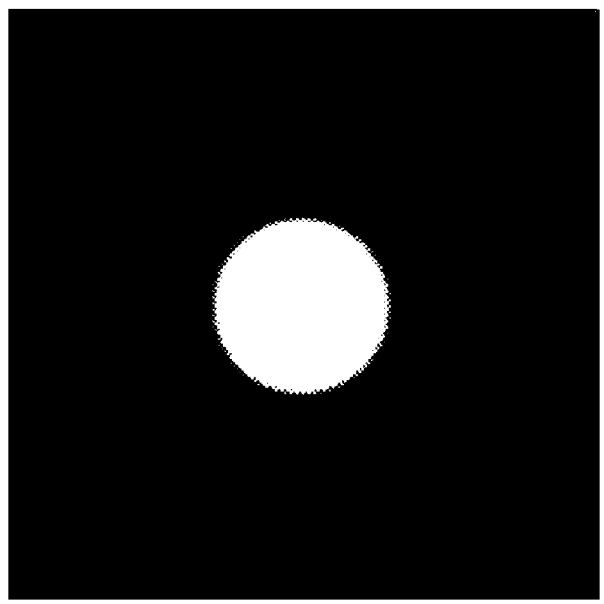

A schematic view at the time of detecting the foreign material T1 on the upper surface using the detecting apparatus 1000 according to an exemplary embodiment of the present invention is shown in FIG. 7, and photographed images of foreign materials detected through the first and second detecting parts 200 and 300 at the time of detecting the foreign material T1 on the upper surface are shown in FIGS. 8a and 8b.

As shown, since the P-polarized light and the S-polarized light scattered through the foreign material T1 on the upper surface of the substrate S do not have a light loss due to transmission, the brightness of the P-polarized light detected by the first detecting part 200 and the brightness of the S-polarized light detected by the second detecting part 300 are the same as each other, and a photographed image (FIG. 8a) of the P-polarized light of the first detecting part 200 and a photographed image (FIG. 8b) of the S-polarized light of the second detecting part 300 are also displayed by bright colors, respectively.

Figure 9:
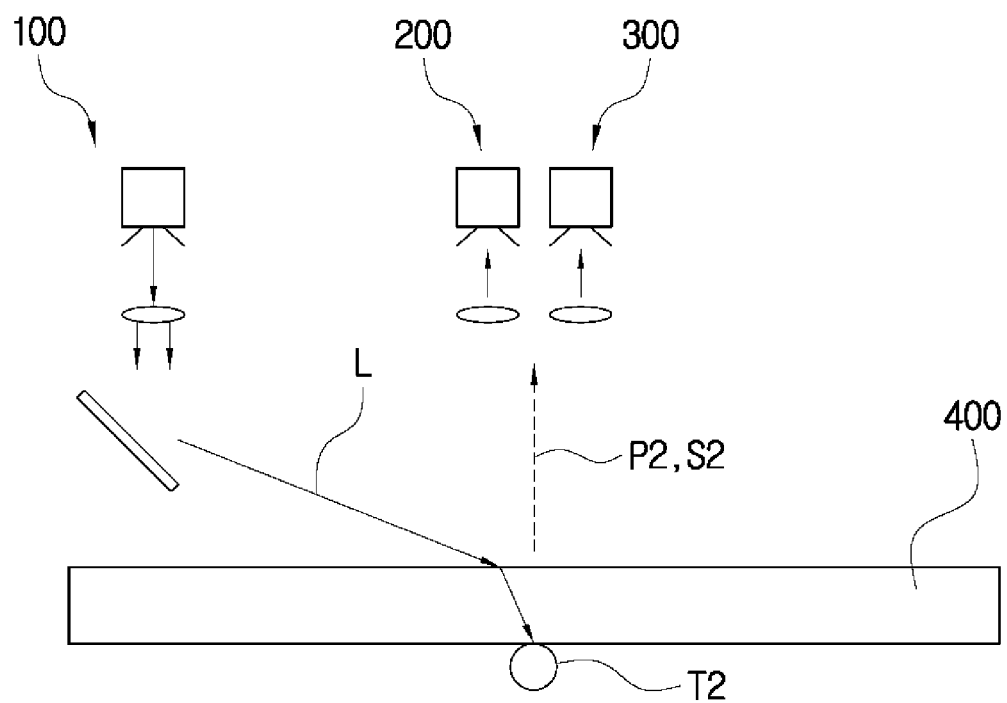
FIG. 9 is a schematic view at the time of detecting the foreign material on the lower surface using the detecting apparatus according to an exemplary embodiment of the present invention.
Figure 10A:
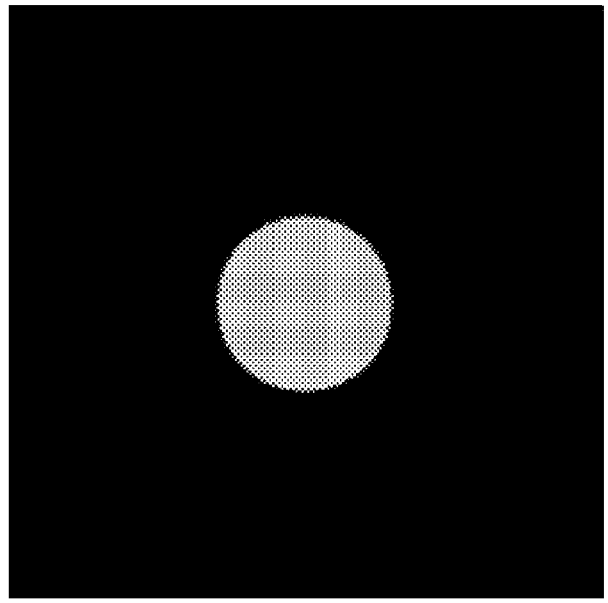
FIGS. 10a and 10b are photographed images of foreign materials detected through a P-polarized light detector and an S-polarized light detector at the time of detecting the foreign material on the lower surface.
Figure 10B:
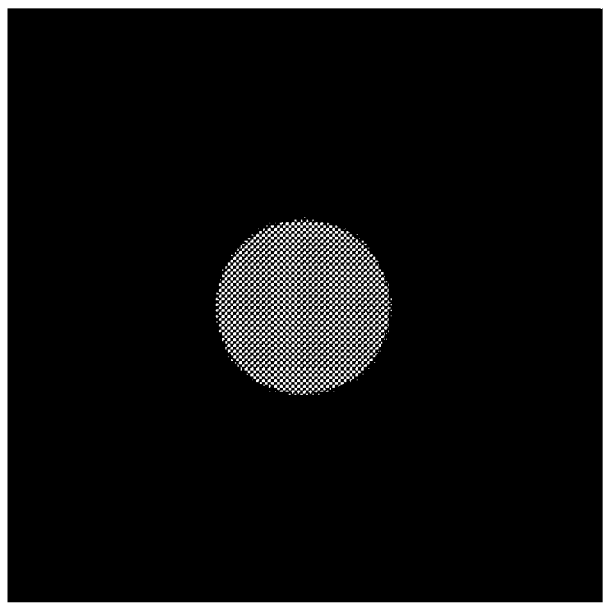

A schematic view at the time of detecting the foreign material on the lower surface using the detecting apparatus 1000 according to an exemplary embodiment of the present invention is shown in FIG. 9, and photographed images of foreign materials detected through the first and second detecting parts 200 and 300 at the time of detecting the foreign material T2 on the lower surface are shown in FIGS. 10a and 10b.

On the other hand, the P-polarized light and the S-polarized light scattered through the foreign material T2 on the lower surface of the substrate S are scattered in the state in which they are transmitted through the substrate S, such that light losses occur. Therefore, the brightness of the P-polarized light detected by the first detecting part 200 and the brightness of the S-polarized light detected by the second detecting part 300 are different from each other due to a difference between the light losses, and a photographed image (FIG. 10a) of the P-polarized light of the first detecting part 200 and a photographed image (FIG. 10b) of the S-polarized light of the second detecting part 300 are displayed by dark colors, respectively.

Additionally, the detecting apparatus 1000 according to the present invention may limit an incident angle at which the light is incident to the substrate S to 65 to 80 degrees, more preferably, 73 degrees in order to maximize a difference between the brightnesses of the P-polarized light and the S-polarized light scattered through the foreign material T2 on the lower surface of the substrate S.

Next, a method of detecting a foreign material on an upper surface using the apparatus 1000 of detecting a foreign material on an upper surface of a transparent substrate using polarized light according to the present invention configured as described above will be described with reference to the accompanying drawings.

First, a step of irradiating light having a predetermined incident angle to the substrate S is performed. The incident angle may be 65 to 80 degrees as described above, more preferably, 73 degrees. The light may be non-polarized light or be linearly polarized light in order to increase strength of a light amount. In the case in which the light is the linearly polarized light, a step of adjusting a polarized light angle of the linearly polarized light may be further performed.

Next, a step of correcting a P-polarized light detector detecting the P-polarized light and an S-polarized light detector detecting the S-polarized light is performed. In detail, a step of correcting the P-polarized light detector and the S-polarized light detector so that the brightnesses of the P-polarized light and the S-polarized light scattered on the upper surface of the substrate become the same as each other is performed. This is to compensate for a fine difference between the brightnesses of the P-polarized light and the S-polarized light that may occur due to the incident angle of the light and a distance difference between the P-polarized light detector and the S-polarized light detector and the foreign material.

Next, a step of detecting each of the P-polarized light and the S-polarized light in the scattered light in the case in which the light irradiated to the substrate S is scattered by the foreign material attached onto the substrate S, such that the scattered light is generated, is performed. In order to detect each of the P-polarized light and the S-polarized light, a P-polarized light plate may be installed in any one of a pair of light detectors, and an S-polarized light plate may be installed in the other of pair of light detectors. In another exemplary embodiment, the scattered light may be split into the P-polarized light and S-polarized light by a polarized light beam splitter, and the P-polarized light and S-polarized light may be irradiated to the pair of light detectors, respectively.

Next, a step of comparing the brightness of the P-polarized light and the brightness of the S-polarized light with each other to distinguish the foreign material attached onto the upper surface of the substrate S and the foreign material attached onto the lower surface of the substrate S from each other is performed.

In detail, in the case in which the brightness of the P-polarized light and the brightness of the S-polarized light are the same as each other, it is judged that the foreign material is the foreign material attached onto the upper surface of the substrate S, and in the case in which the brightness of the S-polarized light is darker than that of the P-polarized light, it is judged that the foreign material is the foreign material attached onto the lower surface of the substrate S.

The present invention should not be construed to being limited to the above-mentioned exemplary embodiment. The present invention may be applied to various fields and may be variously modified by those skilled in the art without departing from the scope of the present invention claimed in the claims. Therefore, it is obvious to those skilled in the art that these alterations and modifications fall in the scope of the present invention.

What is claimed is:

1. A method of detecting a foreign material on an upper surface of a transparent substrate using polarized light comprising:
   irradiating light having a predetermined incident angle to the transparent substrate;
   detecting a P-polarized component of the scattered light of foreign materials attached onto the transparent substrate by the irradiated light;
   detecting an S-polarized component of the scattered light of the foreign materials attached onto the transparent substrate by the irradiated light;
   comparing a brightness of the P-polarized component and a brightness of the S-polarized component with each other to distinguish the foreign material attached onto the upper surface of the transparent substrate and a foreign material attached onto a lower surface of the transparent substrate from each other; and
   removing the foreign material attached onto the lower surface of the transparent substrate,
   wherein in the case in which the brightness of the P-polarized component and the brightness of the S-polarized component are the same as each other, it is judged that the foreign material is the foreign material attached onto the upper surface of the transparent substrate, and in the case in which the brightness of the S-polarized component is darker than that of the P-polarized component, it is judged that the foreign material is the foreign material attached onto the lower surface of the transparent substrate.

2. The method of detecting a foreign material on an upper surface of a transparent substrate using polarized light according to claim 1, further comprising correcting a P-polarized component detector detecting the P-polarized component and an S-polarized component detector detecting the S-polarized component so that the brightnesses of the P-polarized component and the S-polarized component scattered on the upper surface of the transparent substrate become the same as each other, wherein correction is performed for a case of foreign material attached onto the upper surface only.

3. The method of detecting a foreign material on an upper surface of a transparent substrate using polarized light according to claim 1, wherein the incident angle of the light irradiated to the transparent substrate is 65 to 80 degrees, and wherein the incident angle is measured from a perpendicular axis out of the upper surface.

* * * * *